United States Patent [19]
Grendahl

[11] Patent Number: 4,781,717
[45] Date of Patent: Nov. 1, 1988

[54] INTRAOCULAR LENS

[76] Inventor: Dennis T. Grendahl, Excelsior Bay Gables, Excelsior, Minn. 55331

[21] Appl. No.: 60,528

[22] Filed: Jun. 11, 1987

Related U.S. Application Data

[63] Continuation of Ser. No. 758,320, Jul. 24, 1985, abandoned.

[51] Int. Cl.$^4$ .............................................. A61F 2/16
[52] U.S. Cl. .............................................. 623/6
[58] Field of Search ............................................ 623/6

[56] References Cited

U.S. PATENT DOCUMENTS

| | | | |
|---|---|---|---|
| 4,424,597 | 1/1984 | Schlegel | 623/6 |
| 4,596,578 | 6/1986 | Kelman | 623/6 |
| 4,605,409 | 8/1986 | Kelman | 623/6 |

FOREIGN PATENT DOCUMENTS 2124500A 2/1984 United Kingdom ............... 623/6

OTHER PUBLICATIONS

The Rayner Choyce Mark VIII Anterior Chamber Implant, catalogue No. 469, Rayner & Keller Limited, Sheraton House, Chorleywood, Hertfordshire, England (3 pp.), received in PTO Jul. 31, 1978.
Psuedophakos (Book) by Norman S. Jaffe et al, The C. V. Mosby Company, Saint Louis, 1978, pp. 35-37.

*Primary Examiner*—Ronald L. Frinks
*Attorney, Agent, or Firm*—Hugh D. Jaeger

[57] ABSTRACT

A rimmed intraocular lens including an optic and a rim about the lens optic which has a finite width and height of a geometrical cross section. The rim provides for capture of the lens optic in the capsular bag and prevents the cutting or wearing through of the capsular bag. The rim can be attached to a meniscus lens optic, a bi-convex optic, or a plano-convex optic. The rim can be positioned up, equal, or down with respect to the planar access of the lens optic. The rim can be of the same material as the lens optic, or it can be of a different material to preclude edge effect and glare and joined to the lens optic.

6 Claims, 5 Drawing Sheets

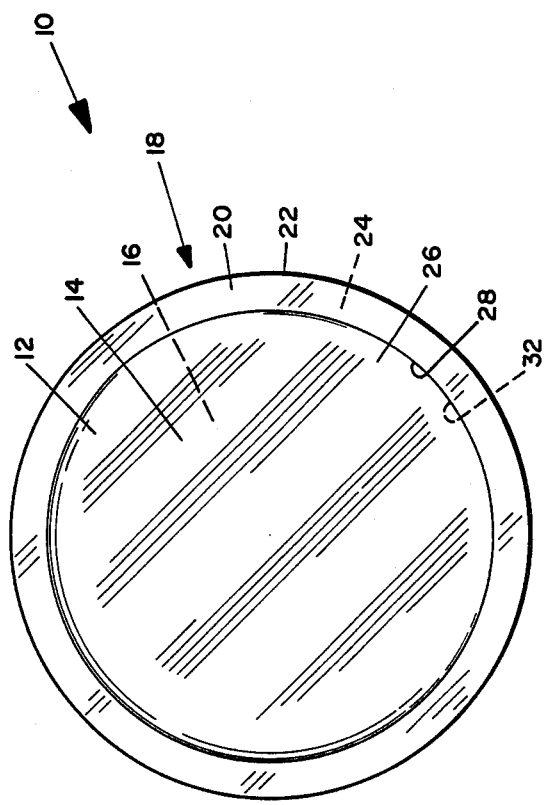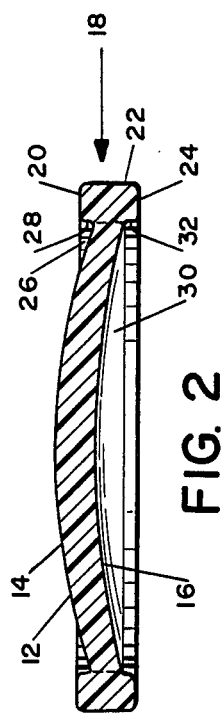

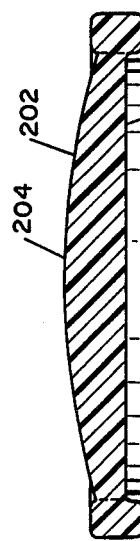

INTRAOCULAR LENS

This application is a continuation of application Ser. No. 758,320, filed July 24, 1985, and now abandoned.

BACKGROUND OF THE INVENTION

1. Field of the Invention

The present invention pertains to an intraocular lens, and more particularly, pertains to an intraocular lens including an encompassing rim of a predetermined geometrical cross section. The rim surrounds an entire edge of the lens optic.

2. Description of the Prior Art

Prior art posterior chamber lenses have sometimes cut or worn through the equator of the capsular bag. The reason for cutting or wearing through is that the edge of the lens optic, while being smooth, was not of a sufficient width to prevent the edge from cutting or wearing through the equator or other point of contact with of the capsular bag.

The present invention overcomes the disadvantages of the prior art by providing an intraocular lens with a rim of a sufficient width to prevent the edge from cutting or wearing through the equator of the capsular bag.

SUMMARY OF THE INVENTION

The general purpose of the present invention is to provide an intraocular lens with a rim for positioning the lens in the capsular bag. The rim is of a finite width, height and geometrical cross section so as not only to secure the rim of the lens within the capsular bag, but to further prevent any cutting or wearing through the equator or other point of contact with of the capsular bag.

According to one embodiment of the present invention, there is provided a unitary, monolithic, self-positioning intraocular lens including a lend optic element and a continuous, unbroken rim element immediately surrounding the lens optic element. The rim element, in cross section extends over and below the edge of the lens optic element and is provided with rounded edges. The rim includes a finite height and width of a predetermined geometrical cross section, such as what one might equate as an oval, an avoid, or an off center ovoid positioned about an edge of a lens optic defining an ellipse between the posterior surface and anterior surface of a lens optic. The rim can either be lathe cut as part of the lens optic, compression molded to the edge of the lens optic, or injection molded as a one piece lens. The rim could also be ultrasonically bonded, such as by a sleeve, and can be of a different color or different material than the lens optic to minimize any light edge effect. For instance, while the lens optic might be polysulfone, the sleeve could be polymethylmethacrylate or vice versa. The rim can be positioned at a central position, an upper position or a lower position with respect to the edge of the lens optic.

One significant aspect and feature of the present invention is an intraocular lens with any type of lens optic, such as bi-convex, plano-convex, meniscus of a concave-convex surface, or like lens optical with a rim positioned about the edges or about at least one edge of the lens optic.

An additional aspect and feature of the present invention is an intraocular lens using a colored rim to minimize or eliminate edge effect and glare reduction caused by light.

Having thus described embodiments of the present invention, it is the principal object hereof to provide a rimmed intraocular lens. The rim of the intraocular lens can assume any predetermined geometrical configuration, such as an ovoid, an oval, or the like.

One object of the present invention is a lend optic, including a rim, where the rim can be lathe cut from either a continuous piece or composite piece of material, the rim can be compression molded onto the lens optic, the rim can be injection molded as one piece to the lens optic, or the rim can be ultrasonically welded or other like process to the lens optic.

Another object of the present invention is a lens including a colored rim where the rim inhibits or eliminates edge effect and reduces glare caused by light.

BRIEF DESCRIPTION OF THE DRAWINGS

FIG. 1 illustrates a plan view of an intraocular lens with a rim, the present invention;

FIG. 2 illustrates a cross-sectional view of FIG. 1;

FIG. 5 illustrates a cross-sectional view of an alternative embodiment;

FIG. 6 illustrates a cross-sectional view of another alternative embodiment;

DESCRIPTION OF THE PREFERRED EMBODIMENTS

Figure 3:
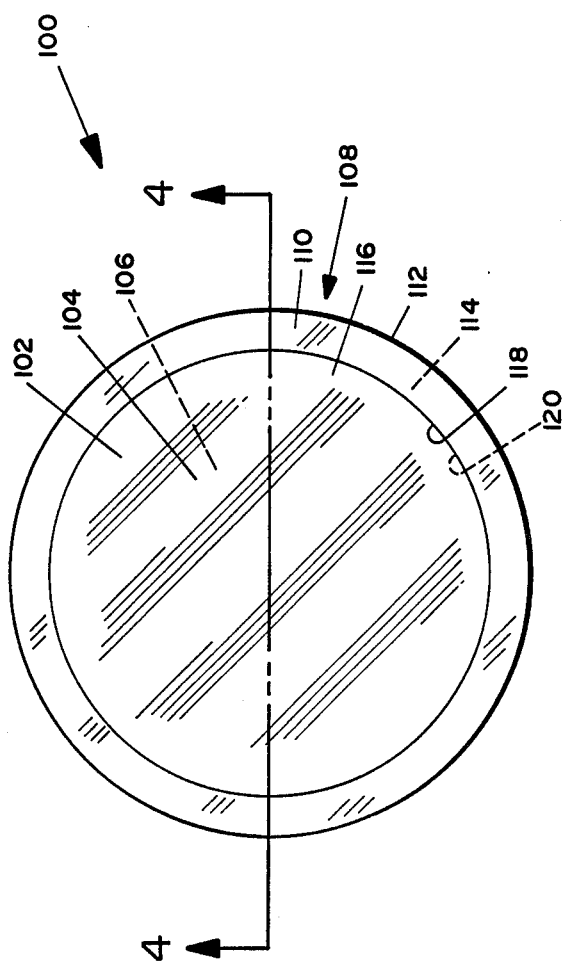
FIG. 3 illustrates a plan view of a first alternative embodiment.

FIG. 1 illustrates a plan view of a rimmed intraocular lens 10, the present invention, including an optic 12, a convex anterior surface 14, and a concave posterior surface 16 surrounded by a rim 18. The rim 18 includes a rim top 20, a rim edge 22, and a rim bottom 24. There is provided an anterior space 26 between the convex anterior surface 14 and an inner upper rim surface 29; and, as shown in FIG. 2 there is a concave posterior space 30 between an inner, lower rim surface 32 and the posterior concave surface 16. The edges of the rim are rounded accordingly. The rim 18 can be made of a colored material such as blue polymethylmethacrylate or blue polysulfone shown adjacent, by the use of dashed lines, to the optic 12 and are shown through FIGS. 1–10. The lens can be provided with or without loops for implant in either the posterior or anterior chamber.

FIG. 2 illustrates a cross-sectional embodiment of FIG. 1 where all numerals correspond to those elements previously described. Specifically, the geometrical cross section of the rim is illustrated, which is substantially square or rectangular in nature with rounded edges. While in this particular example the rim has been illustrated as a continuous piece of material with respect to the lens optic, such as being compression molded, injection molded, or lather cut, the rim could also be of a composite material, such as being lathe cut, or could be of a different material and ultrasonically welded or joined by other like process to the lens optic. The particular example shown in FIG. 2 is not to be construed as limiting of the present invention, but is by way of example and for purposes of illustration only. In this particular example, the rim is illustrated as a continuous member to a meniscus lens optic. While the rim could have very well have been injection molded or compression molded or even lathe cut about the lens optic, the rim could also be ultrasonically welded to the lens optic. Also, the lens optic could be a composite material with respect to the rim, such that the lens optic could be colored differently, such as clear or with ultraviolet absorber compared to the rim, which could be a blue or green color, out of a composite material for reduction of edge effect and glare. The alternatives are within the teachings and scope of the present invention, although not all of the alternatives are illustrated for the sake of brevity.

Figure 4:
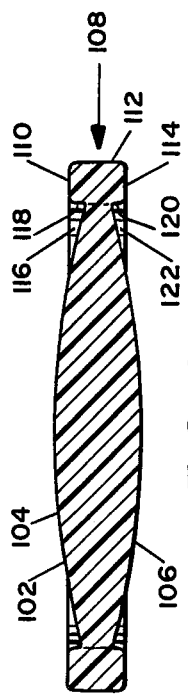
FIG. 4 illustrates a cross-sectional view of FIG. 3.

FIG. 3 illustrates an alternative embodiment of a rimmed intraocular lens 100 of the present invention, including a lens optic 102 of a convex anterior surface 104 and a convex posterior surface 106 with a rim 108 about the two surfaces. The rim 108 includes a rim top 110, a rim edge 112, and a rim bottom 114. An equally spaced inner, upper rim surface 118 and an inner, lower rim surface 120 are about an anterior space 116 and a posterior space 122 formed with convex anterior surface 104 and convex posterior surface 106, respectively, as shown in FIG. 4. These spaces are equal by way of example and for purposes of illustration only, but the optic can be either moved upwardly with respect to the rim, as illustrated in FIG. 5 with respect to FIG. 4, or in a reverse manner, downwardly with respect to the rim.

FIG. 4 illustrates a cross-sectional view of FIG. 3 where all numerals correspond to those elements previously described. The concepts of the present invention, as disclosed in FIGS. 3 and 4, are those of FIGS. 1 and 2 with the exception that FIGS. 3 and 4 are illustrated by a bi-convex optic.

FIG. 5 illustrates a cross-sectional view of an alternative embodiment, the lens optic 150 similar to FIGS. 3 and 4 where the lens optic has been moved upwardly providing an inner, upper space which is of less height than a lower space.

FIG. 6 illustrates a cross-sectional view of an alternative embodiment of a lens optic 200, similar to that of FIG. 5, with a plano-convex optic 202, including a convex anterior surface 204 and a plano posterior surface 206 which have been substituted for the bi-convex optic 102 of FIG. 4. All other numerals correspond to those elements previously described.

Figure 7:
FIG. 7 illustrates a cross-sectional view of an additional embodiment.

FIG. 7 illustrates a cross-sectional view of an additional alternative embodiment 250 of a plano-convex rimmed lens where the convex anterior surface and the plano posterior surface are equally spaced with respect to the top and bottom of the sides of the rim.

ALTERNATIVE EMBODIMENTS OF RIMS

Figure 8:
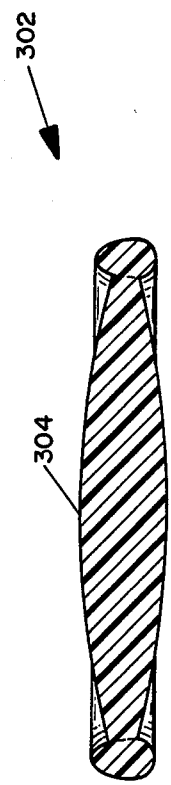
FIG. 8 illustrates a cross-sectional view of an ovoid rim.

FIG. 8 illustrates a cross-sectional view of an ovoid rim 302 about a lens optic 304.

Figure 9:
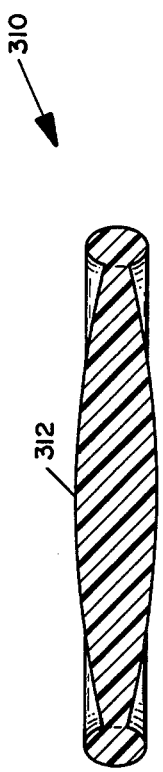
FIG. 9 illustrates a cross-sectional view of an oval rim.

FIG. 9 illustrates a cross-sectional view of an oval rim 310 about lens optic 312.

Figure 10:
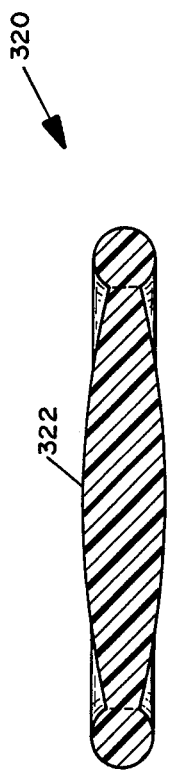
FIG. 10 illustrates a cross-sectional view of a round rim.

FIG. 10 illustrates a cross-sectional view of a rounded rim 320 defining a circle about a lens optic 322.

It is claimed:

1. A unitary, monolithic, self-positioning intraocular lens for implantation in the capsular bag of the human eye, the lens comprising:
   a. a lens optic element; and,
   b. a continuous, unbroken rim element immediately surrounding said optic element, said rim element, in cross section, extending over and below the edge of said optic element said rim element having a width and height of a geometric cross section provided with rounded edges so as to secure the rim within the capsular bag and prevent cutting or wearing through the equator of the capsular bag, and said rim being of a different color than said lens optic whereby edge effect and glare are minimized or eliminated.

2. The lens of claim 1 wherein said rim element cross section defines a square or rectangle with rounded corners.

3. The lens of claim 1 wherein said rim element cross section defines an oval.

4. The lens of claim 1 wherein said rim element cross section defines a circle.

5. The lens of claim 1 wherein the rim element is blue.

6. The lens of claim 1 wherein said rim element cross-section defines an ellipse.

* * * * *